(12) United States Patent
Geytenbeek et al.

(10) Patent No.: US 11,753,435 B2
(45) Date of Patent: Sep. 12, 2023

(54) PROCESS

(71) Applicant: Avecho Biotechnology Limited, Clayton (AU)

(72) Inventors: Stephen Geytenbeek, Clayton (AU); Andrew Stirling, Clayton (AU); Paul David Gavin, Clayton (AU)

(73) Assignee: Avecho Biotechnology Limited, Victoria (AU)

( * ) Notice: Subject to any disclaimer, the term of this patent is extended or adjusted under 35 U.S.C. 154(b) by 0 days.

(21) Appl. No.: 17/552,188

(22) Filed: Dec. 15, 2021

(65) Prior Publication Data

US 2022/0106353 A1 Apr. 7, 2022

Related U.S. Application Data

(63) Continuation of application No. 16/470,943, filed as application No. PCT/AU2017/051381 on Dec. 13, 2017, now abandoned.

(30) Foreign Application Priority Data

Dec. 21, 2016 (AU) .................................. 2016905298

(51) Int. Cl.
*C07J 51/00* (2006.01)
*C07F 9/09* (2006.01)

(52) U.S. Cl.
CPC .................. *C07J 51/00* (2013.01); *C07F 9/09* (2013.01); *C07F 9/095* (2013.01)

(58) Field of Classification Search
CPC .............. C07J 51/00; C07F 9/09; C07F 9/095
See application file for complete search history.

(56) References Cited

U.S. PATENT DOCUMENTS

| | | |
|---|---|---|
| 2,407,823 A | 9/1946 | Fieser |
| 2,457,932 A | 1/1949 | Solmssen et al. |
| 2,667,479 A | 1/1954 | Hoffman et al. |
| 2,913,477 A | 11/1959 | Hirschmann |
| 3,127,434 A | 3/1964 | Andrews |
| 3,212,901 A | 10/1965 | Robeson |
| 3,607,765 A | 9/1971 | Wixon |
| 4,075,333 A | 2/1978 | Josse |
| 4,141,938 A | 2/1979 | Klose |
| 4,299,906 A | 11/1981 | Liu |
| 4,369,172 A | 1/1983 | Schor et al. |
| 4,444,755 A | 4/1984 | Horrobin |
| 4,603,142 A | 7/1986 | Burger et al. |
| 4,654,373 A | 3/1987 | Bertelli |
| 4,684,520 A | 8/1987 | Bertelli |
| 4,686,211 A | 8/1987 | Hara et al. |
| 4,874,883 A | 10/1989 | Uphues et al. |
| 4,952,495 A | 8/1990 | Belly et al. |
| 4,977,282 A | 12/1990 | Baldwin et al. |
| 5,041,434 A | 8/1991 | Lubkin |
| 5,053,222 A | 10/1991 | Takasu et al. |
| 5,091,848 A | 2/1992 | Kojima |
| 5,094,848 A | 3/1992 | Brixner |
| 5,114,957 A | 5/1992 | Hendler et al. |
| 5,138,084 A | 8/1992 | Casagrande et al. |
| 5,173,304 A | 12/1992 | Lohner et al. |
| 5,334,378 A | 8/1994 | Mitani et al. |
| 5,374,645 A | 12/1994 | Kurihara-Bergstrom et al. |
| 5,387,579 A | 2/1995 | Meybeck et al. |
| 5,446,070 A | 8/1995 | Mantelle |
| 5,474,891 A | 12/1995 | Murphy |
| 5,474,991 A | 12/1995 | Ogata et al. |
| 5,554,781 A | 9/1996 | Reierson |
| 5,570,504 A | 11/1996 | Distefano et al. |
| 5,583,105 A | 12/1996 | Kovacs et al. |
| 5,589,504 A | 12/1996 | Dannenberg et al. |
| 5,603,949 A | 2/1997 | Meybeck et al. |
| 5,607,921 A | 3/1997 | Bernard et al. |
| 5,643,597 A | 7/1997 | Meybeck et al. |
| 5,656,618 A | 8/1997 | Meybeck et al. |
| 5,656,672 A | 8/1997 | Collin et al. |
| 5,741,518 A | 4/1998 | Ribier et al. |
| 5,759,526 A | 6/1998 | Simonnet et al. |
| 5,776,915 A | 7/1998 | Peterson et al. |
| 5,780,504 A | 7/1998 | Ptchelintsev |
| 5,804,168 A | 9/1998 | Murad |
| 5,804,216 A | 9/1998 | Terren et al. |
| 5,807,542 A | 9/1998 | Challis et al. |
| 5,807,845 A | 9/1998 | Ogata et al. |
| 5,885,595 A | 3/1999 | Corey et al. |
| 5,906,811 A | 5/1999 | Hersh |
| 5,908,846 A | 6/1999 | Bundgaard et al. |

(Continued)

FOREIGN PATENT DOCUMENTS

| CA | 1337992 C | 1/1996 |
|---|---|---|
| CA | 2426852 A1 | 5/2002 |

(Continued)

OTHER PUBLICATIONS

Aberg, F. et al., "Distribution and redox state of ubiquinones in rat and human tissues," Arch. Biochem. Biophys. (1992) 295(2):230-234.

Advantages of Liposomal Delivery Systems for Anthracyclines, Semin. Oncol., 2004, 6 Suppl 13, 5-15.

Almeida, M.E.M. et al., "Evaluation of soybean oil deodorization distillate for Vitamin E recovery," Arq. Biol. Tecnol. (1994) 37(4):1003-1011.

Anslyn, E.V. et al., "Solutions and Non-Covalent Binding Forces," Modern Physical Organic Chemistry. Chapter 3. University Science Books. (2006) see p. 146.

Baker et al., "Propofol," Anesthesiology, 2005, 103: 860-876.

BarreTT, C.W. et al., "The effect of particle size and vehicle on the percutaneous absorption of fluocinolone acetonide," Brit. J. Dermatol. (1965) 77:576-578.

(Continued)

*Primary Examiner* — Timothy R Rozof
(74) *Attorney, Agent, or Firm* — Michael Best & Friedrich LLP

(57) ABSTRACT

An efficient and commercial phosphorylation process of a complex alcohol, such as secondary and tertiary alcohols, with $P_4O_{10}$ at high temperatures, and a product obtained by the process.

7 Claims, No Drawings

(56) References Cited

U.S. PATENT DOCUMENTS

| | | |
|---|---|---|
| 5,916,915 A | 6/1999 | Hong et al. |
| 5,928,631 A | 7/1999 | Lucas et al. |
| 5,952,361 A | 9/1999 | Dias Nahoum |
| 5,952,373 A | 9/1999 | Lanzendorfer et al. |
| 5,965,750 A | 10/1999 | Oonishi et al. |
| 5,981,474 A | 11/1999 | Manning et al. |
| 5,985,856 A | 11/1999 | Stella et al. |
| 6,022,867 A | 2/2000 | Ito et al. |
| 6,028,105 A | 2/2000 | Nigra |
| 6,046,181 A | 4/2000 | Oonishi et al. |
| 6,048,891 A | 4/2000 | Wechter |
| 6,096,326 A | 8/2000 | Wikholm |
| 6,121,249 A | 9/2000 | Weissman et al. |
| 6,143,770 A | 11/2000 | Lane et al. |
| 6,184,247 B1 | 2/2001 | Schneider |
| 6,231,885 B1 | 5/2001 | Carrara |
| 6,248,758 B1 | 6/2001 | Klokkers et al. |
| 6,248,779 B1 | 6/2001 | Shimizu et al. |
| 6,361,800 B1 | 3/2002 | Cooper et al. |
| 6,384,043 B1 | 5/2002 | Peyman et al. |
| 6,403,811 B1 | 6/2002 | West |
| 6,417,223 B1 | 7/2002 | Sanders et al. |
| 6,423,742 B1 | 7/2002 | Larson |
| 6,444,220 B2 | 9/2002 | Wiley |
| 6,444,234 B1 | 9/2002 | Kirby et al. |
| 6,479,540 B1 | 11/2002 | Constantinides et al. |
| 6,485,950 B1 | 11/2002 | Kumar et al. |
| 6,503,545 B1 | 1/2003 | Perlman et al. |
| 6,579,995 B1 | 6/2003 | West |
| 6,599,933 B2 | 7/2003 | Takada et al. |
| 6,641,847 B1 | 11/2003 | Nawar |
| 6,645,998 B2 | 11/2003 | Sanders et al. |
| 6,703,384 B2 | 3/2004 | Sanders et al. |
| 6,727,280 B2 | 4/2004 | Paiepu et al. |
| 6,770,672 B1 | 8/2004 | Sanders et al. |
| 6,887,648 B2 | 5/2005 | Pavelchek et al. |
| 7,074,825 B2 | 7/2006 | Mo et al. |
| 7,179,486 B1 | 2/2007 | Mulye |
| 7,648,710 B2 | 1/2010 | West |
| 8,008,345 B2 | 8/2011 | West et al. |
| 8,529,947 B2 | 9/2013 | West et al. |
| 8,546,453 B2 | 10/2013 | Zhang |
| 8,652,511 B2 | 2/2014 | Cottrell et al. |
| 9,314,527 B2 | 4/2016 | Cottrell et al. |
| 9,561,243 B2 | 2/2017 | Libinaki et al. |
| 2001/0006659 A1 | 7/2001 | Koike et al. |
| 2001/0044462 A1 | 11/2001 | Hensley et al. |
| 2002/0045765 A1 | 4/2002 | Kim et al. |
| 2002/0127198 A1 | 9/2002 | Rothbard et al. |
| 2002/0131994 A1 | 9/2002 | Schur et al. |
| 2002/0132845 A1 | 9/2002 | Miller et al. |
| 2002/0151467 A1 | 10/2002 | Leung |
| 2003/0035812 A1 | 2/2003 | Ito et al. |
| 2003/0109575 A1 | 6/2003 | Lambert et al. |
| 2003/0157326 A1 | 8/2003 | Vaghefi et al. |
| 2003/0206972 A1 | 11/2003 | Babish et al. |
| 2003/0220301 A1 | 11/2003 | Lal et al. |
| 2004/0052745 A1 | 3/2004 | Bernard et al. |
| 2004/0052754 A1 | 3/2004 | West et al. |
| 2004/0062817 A1 | 4/2004 | Peshoff |
| 2004/0067890 A1 | 4/2004 | Gupta |
| 2004/0097431 A1 | 5/2004 | Sanders et al. |
| 2004/0097472 A1 | 5/2004 | West et al. |
| 2004/0102385 A1 | 5/2004 | Ames et al. |
| 2004/0131569 A1 | 7/2004 | Schneider et al. |
| 2004/0167081 A1 | 8/2004 | Abbruzzese et al. |
| 2004/0204343 A1 | 10/2004 | Fishman |
| 2004/0234602 A1 | 11/2004 | Fischer et al. |
| 2004/0235938 A1 | 11/2004 | Sanders et al. |
| 2004/0241225 A1 | 12/2004 | West |
| 2005/0009787 A1 | 1/2005 | West et al. |
| 2005/0089495 A1 | 4/2005 | West |
| 2005/0134664 A1 | 6/2005 | Pavlin |
| 2005/0142174 A1 | 6/2005 | Assmus et al. |
| 2005/0220733 A1 | 10/2005 | Tsuzuki et al. |
| 2006/0120979 A1 | 6/2006 | Rubin |
| 2006/0228395 A1 | 10/2006 | Lamb et al. |
| 2006/0241085 A1 | 10/2006 | West et al. |
| 2006/0257459 A1 | 11/2006 | West et al. |
| 2006/0281715 A1 | 12/2006 | West |
| 2006/0281716 A1 | 12/2006 | West et al. |
| 2007/0042999 A1 | 2/2007 | West et al. |
| 2007/0110739 A1 | 5/2007 | Logsdon |
| 2007/0135390 A1 | 6/2007 | West et al. |
| 2007/0141090 A1 | 6/2007 | Harris et al. |
| 2007/0141133 A1 | 6/2007 | Wang et al. |
| 2007/0224253 A1 | 9/2007 | Franklin |
| 2008/0233178 A1 | 9/2008 | Reidenberg et al. |
| 2008/0254073 A1 | 10/2008 | Chi |
| 2008/0299100 A1 | 12/2008 | Hsia et al. |
| 2009/0004166 A1 | 1/2009 | West et al. |
| 2009/0005348 A1 | 1/2009 | Ogru et al. |
| 2009/0036354 A1 | 2/2009 | Gavin et al. |
| 2009/0104258 A1 | 4/2009 | Dumas et al. |
| 2009/0186856 A1 | 7/2009 | West et al. |
| 2009/0233881 A1 | 9/2009 | West et al. |
| 2009/0239827 A1 | 9/2009 | Ogru et al. |
| 2009/0274677 A1 | 11/2009 | Isaacs et al. |
| 2009/0319191 A1 | 12/2009 | Rivas et al. |
| 2009/0325953 A1 | 12/2009 | Sahoo et al. |
| 2009/0325974 A1 | 12/2009 | Eggenweiler et al. |
| 2010/0034880 A1 | 2/2010 | Sintov et al. |
| 2010/0076094 A1 | 3/2010 | West et al. |
| 2010/0222305 A1 | 9/2010 | West et al. |
| 2010/0261670 A1 | 10/2010 | West et al. |
| 2011/0003774 A1 | 1/2011 | West et al. |
| 2012/0202780 A1 | 8/2012 | Gavin et al. |
| 2012/0283233 A1 | 11/2012 | Gavin et al. |
| 2012/0321604 A1 | 12/2012 | Libinaki |
| 2014/0322330 A1 | 10/2014 | Chiragkumar |
| 2016/0184436 A1 | 6/2016 | Cottrell et al. |
| 2016/0331838 A1 | 12/2016 | Gavin et al. |
| 2016/0375136 A1 | 12/2016 | Gavin et al. |
| 2017/0112863 A1 | 4/2017 | Libinaki et al. |

FOREIGN PATENT DOCUMENTS

| | | |
|---|---|---|
| CA | 2426885 A1 | 5/2002 |
| CN | 1600297 A | 3/2005 |
| CN | 1917858 A | 2/2007 |
| CN | 101524330 A | 9/2009 |
| CN | 102079756 B | 9/2012 |
| EP | 0171009 B1 | 2/1986 |
| EP | 0324387 B1 | 7/1989 |
| EP | 0338429 B1 | 10/1989 |
| EP | 0430045 B1 | 6/1991 |
| EP | 0430336 B1 | 6/1991 |
| EP | 0436911 A2 | 7/1991 |
| EP | 0565007 B1 | 10/1993 |
| EP | 0574255 B1 | 12/1993 |
| EP | 0612521 A1 | 8/1994 |
| EP | 0617963 B1 | 10/1994 |
| EP | 0641790 A1 | 3/1995 |
| EP | 0643969 B1 | 3/1995 |
| EP | 0650721 A1 | 5/1995 |
| EP | 0661053 A1 | 7/1995 |
| EP | 0669132 A1 | 8/1995 |
| EP | 0674904 A1 | 10/1995 |
| EP | 0679399 B1 | 11/1995 |
| EP | 0680760 A1 | 11/1995 |
| EP | 0681840 B1 | 11/1995 |
| EP | 0684043 A1 | 12/1995 |
| EP | 0699437 A1 | 3/1996 |
| EP | 0699440 A1 | 3/1996 |
| EP | 0826365 A2 | 3/1998 |
| EP | 0845216 A1 | 6/1998 |
| EP | 0699437 B1 | 12/1998 |
| EP | 0965328 A1 | 12/1999 |
| EP | 1000541 B1 | 5/2000 |
| EP | 1023897 A2 | 8/2000 |
| EP | 1053749 A1 | 11/2000 |
| EP | 1264595 | 12/2002 |
| EP | 1470817 A1 | 10/2004 |
| EP | 1783209 B1 | 5/2007 |

(56) References Cited

FOREIGN PATENT DOCUMENTS

| | | |
|---|---|---|
| FR | 2777179 A1 | 10/1999 |
| GB | 778142 A | 7/1957 |
| GB | 1121683 A | 7/1968 |
| GB | 2227662 A | 8/1990 |
| JP | 50022535 A | 3/1975 |
| JP | 52039013 | 3/1977 |
| JP | 53015381 | 2/1978 |
| JP | 58180410 A | 10/1983 |
| JP | 59044375 A | 3/1984 |
| JP | 59157091 A | 9/1984 |
| JP | 60197621 A | 10/1985 |
| JP | 61086940 A | 5/1986 |
| JP | 61091137 A | 5/1986 |
| JP | 61176535 A | 8/1986 |
| JP | 61233631 A | 10/1986 |
| JP | 62195393 A | 8/1987 |
| JP | 63093791 A | 4/1988 |
| JP | 63139972 A | 6/1988 |
| JP | 1228920 A | 9/1989 |
| JP | 1274830 A | 11/1989 |
| JP | 03-072426 A | 3/1991 |
| JP | 03-120230 A | 5/1991 |
| JP | 4208209 A | 7/1992 |
| JP | 4270212 A | 9/1992 |
| JP | 05-000946 A | 1/1993 |
| JP | 5132700 B2 | 5/1993 |
| JP | 5201858 A | 8/1993 |
| JP | 6048962 A | 2/1994 |
| JP | 6056699 A | 3/1994 |
| JP | 6078214 B | 10/1994 |
| JP | 7011291 A | 1/1995 |
| JP | 7207298 A | 8/1995 |
| JP | 7278587 A | 10/1995 |
| JP | 7316170 A | 12/1995 |
| JP | 8073338 A | 3/1996 |
| JP | 8193089 A | 7/1996 |
| JP | 08-231564 A | 9/1996 |
| JP | 8311085 A | 11/1996 |
| JP | 8311489 A | 11/1996 |
| JP | 8325594 A | 12/1996 |
| JP | 9044375 A | 2/1997 |
| JP | 9309813 A | 12/1997 |
| JP | 10045783 A | 2/1998 |
| JP | 10155429 A | 6/1998 |
| JP | 10509451 T | 9/1998 |
| JP | 10511677 T | 11/1998 |
| JP | 11043436 A | 2/1999 |
| JP | 11506419 T | 6/1999 |
| JP | 11199424 A | 7/1999 |
| JP | 11199465 A | 7/1999 |
| JP | 2000198701 A | 7/2000 |
| JP | 2001169731 A | 6/2001 |
| JP | 2001247585 A | 9/2001 |
| JP | 2002080475 A | 3/2002 |
| JP | 2002088091 A | 3/2002 |
| JP | 2003128531 A | 5/2003 |
| JP | 2003171313 A | 6/2003 |
| JP | 2006143660 A | 6/2008 |
| NZ | 244549 | 7/1994 |
| RU | 2266121 C2 | 12/2005 |
| RU | 2296743 C2 | 4/2007 |
| RU | 2302857 C2 | 7/2007 |
| RU | 2373957 C2 | 11/2009 |
| RU | 2009125613 A | 1/2011 |
| SU | 925961 | 5/1982 |
| UA | 29476 C2 | 11/2000 |
| WO | WO91/17987 A1 | 11/1991 |
| WO | WO92/03122 A1 | 3/1992 |
| WO | WO92/07544 A1 | 5/1992 |
| WO | WO92/08459 A1 | 5/1992 |
| WO | WO92/15289 A1 | 9/1992 |
| WO | WO93/02661 A1 | 2/1993 |
| WO | WO93/09768 A1 | 5/1993 |
| WO | WO93/15731 A1 | 8/1993 |
| WO | WO93/24131 A1 | 12/1993 |
| WO | WO95/31217 A1 | 11/1995 |
| WO | WO95/34303 A1 | 12/1995 |
| WO | WO96/17852 A1 | 6/1996 |
| WO | WO96/20715 A1 | 7/1996 |
| WO | WO96/21440 A1 | 7/1996 |
| WO | WO96/29336 A1 | 9/1996 |
| WO | WO96/37196 A1 | 11/1996 |
| WO | WO97/02803 A1 | 1/1997 |
| WO | WO97/14705 A1 | 4/1997 |
| WO | WO97/35591 A2 | 10/1997 |
| WO | WO1998/030205 A1 | 7/1998 |
| WO | WO99/35242 A1 | 7/1999 |
| WO | WO99/58555 A2 | 11/1999 |
| WO | WO00/08033 A1 | 2/2000 |
| WO | WO00/16772 A1 | 3/2000 |
| WO | WO00/30620 A1 | 6/2000 |
| WO | WO00/43380 A1 | 7/2000 |
| WO | WO00/44237 A2 | 8/2000 |
| WO | WO00/44375 A1 | 8/2000 |
| WO | WO2000/048571 A1 | 8/2000 |
| WO | WO00/53728 A2 | 9/2000 |
| WO | WO00/57876 A1 | 10/2000 |
| WO | WO00/59475 A1 | 10/2000 |
| WO | WO00/69865 A1 | 11/2000 |
| WO | WO00/71094 A1 | 11/2000 |
| WO | WO00/71125 A2 | 11/2000 |
| WO | WO00/74684 A1 | 12/2000 |
| WO | WO01/13901 A2 | 3/2001 |
| WO | WO01/19372 A1 | 3/2001 |
| WO | WO01/22937 A1 | 4/2001 |
| WO | WO01/35883 A1 | 5/2001 |
| WO | WO01/35998 A1 | 5/2001 |
| WO | WO01/46204 A1 | 6/2001 |
| WO | WO01/54674 A1 | 8/2001 |
| WO | WO01/58889 A1 | 8/2001 |
| WO | WO01/072300 A1 | 10/2001 |
| WO | WO02/02385 A1 | 1/2002 |
| WO | WO02/13810 A1 | 2/2002 |
| WO | WO02/26238 A1 | 4/2002 |
| WO | WO02/36736 A2 | 5/2002 |
| WO | WO02/39996 A2 | 5/2002 |
| WO | WO02/40033 A1 | 5/2002 |
| WO | WO02/40034 A1 | 5/2002 |
| WO | WO2002/045709 A1 | 6/2002 |
| WO | WO2002/096217 A1 | 12/2002 |
| WO | WO03/011303 A1 | 2/2003 |
| WO | WO03/013550 A1 | 2/2003 |
| WO | WO03/024429 A1 | 3/2003 |
| WO | WO03/024430 A1 | 3/2003 |
| WO | WO03/026673 A1 | 4/2003 |
| WO | WO03/039461 A2 | 5/2003 |
| WO | WO03/043570 A2 | 5/2003 |
| WO | WO03/049774 A1 | 6/2003 |
| WO | WO03/053407 A1 | 7/2003 |
| WO | WO03/068209 A1 | 8/2003 |
| WO | WO03/097714 A1 | 11/2003 |
| WO | WO03/101480 A1 | 12/2003 |
| WO | WO2004/010941 A2 | 2/2004 |
| WO | WO2004/014432 A1 | 2/2004 |
| WO | WO2004/060315 A2 | 7/2004 |
| WO | WO2004/064831 A1 | 8/2004 |
| WO | WO2004/091636 A1 | 10/2004 |
| WO | WO2004/092186 A1 | 10/2004 |
| WO | WO2004/092187 A1 | 10/2004 |
| WO | WO2005/023282 A1 | 3/2005 |
| WO | WO2005/084678 A1 | 9/2005 |
| WO | WO2006/012692 A1 | 2/2006 |
| WO | WO2006/041506 A2 | 4/2006 |
| WO | WO2006/092024 A1 | 9/2006 |
| WO | WO2006/092025 A1 | 9/2006 |
| WO | WO2006/133506 A1 | 12/2006 |
| WO | WO2007/070981 A1 | 6/2007 |
| WO | WO2007/075883 A2 | 7/2007 |
| WO | WO2008/034178 A1 | 3/2008 |
| WO | WO2008/073731 A2 | 6/2008 |
| WO | WO2009/146443 A1 | 12/2009 |
| WO | WO2011/075775 A1 | 6/2011 |
| WO | WO2011/094814 A1 | 8/2011 |

(56) References Cited

FOREIGN PATENT DOCUMENTS

| | | |
|---|---|---|
| WO | WO2011/120084 A1 | 10/2011 |
| WO | WO2013/066400 A1 | 5/2013 |
| WO | WO2017/096427 A1 | 6/2017 |

OTHER PUBLICATIONS

Barry, "Novel mechanisms and devices to enable successful transdermal drug delivery," Sciences, 2001; 14:101-114.

Berge et al., "Pharmaceutical Salts," Journal Pharmaceutical Sciences, 66:1-19, 1977.

Bikerman, J.J., "Mechanical destruction of young and old foam films," J. Phys. Chem. (1952) 56:164-165.

Block, L.H., "Chapter 44: Medicated Topicals," in Remington: The Science and Practice of Pharmacy, 20th edition, Edited by Alfonso R. Gennaro, Baltimore, MD, Lippincott, Williams & Wilkins (2000) 836-857.

Blom, J.H. et al., "Reproductive success of female rainbow trout (*Oncorhynchus mykiss*) in response to graded dietary ascorbyl monophosphate levels," Biol. of Reproduction (1995) 52:1073-1080.

Blum, A. et al., "Clinical and inflammatory effects of dietary L-arginine in patients with intractable angina pectoris," Amer. J. Cardiol. (1999) 1488-1489.

Brandt, M., "Steroid hormone biosynthesis," (2002) printed from http://www.rose_hulman.edu/~brandt/Chem430/Steroids.pdf on Nov. 20, 2010 (7 pages).

Cevc, G. "Transdermal drug delivery of insulin with ultradeformable carriers," Clin. Pharmacokinet. (2003) 42(5):461-474.

Cevc, G. et al., "Ultraflexible vesicles, transfersomes, have an extremely low pore penetration resistance and transport therapeutic amounts of insulin across the intact mammalian skin," Biochim. Biophys. Acta (1998) 1368:201-215.

Chae, B. J. et al., "Effects of incremental levels of alpha-tocopherol acetate on performance, nutrient digestibility and meat quality of commercial broilers," Asian Australasian Journal of Animal Sciences, 2006, vol. 19, No. 2, pp. 203-208.

Database WPI—Week 201108, Thomson Scientific, London, GB, AN 2010-N41794 XP002727982 & CN101837 (2010).

De Wolfe, F.A. et al., "Ligand-binding proteins: their potential for application in systems for controlled delivery and uptake of ligands," Pharmacol. Rev. (2000) 52(2):207-236.

Devaraj, S. et al., "Alpha tocopherol supplementation decreases serum C-reactive protein and monocyte interleukin-6 levels in normal volunteers and type 2 diabetic patients," Free Radic. Biol. Med. (2000) 29(8):790-792.

Devaraj, S. et al., "Modulation of monocyte-macrophage function with alpha-tocopherol: implications for atherosclerosis," Nat. Rev. (2002) 60(1):8-14.

Devaraj, S. et la., "Alpha tocopherol decreases CD36 expression in human monocyte-derived macrophages," J. Lipid Res. (2001) 42:521-527.

Dolfi, S. C. et al., "Inhibitory Effects of Different Forms of Tocopherols, Tocopherol Phosphates, and Tocopherol Quinones on Growth of Colon Cancer Cells," Journal of Agricultural and Food Chemistry, 2013, vol. 61, No. 36, pp. 8533-8540.

Ernster, L. et al., "Biochemical, physiological and medical aspects of ubiquinone function," Biochim. Biophys. Acta (1995) 1271:195-204.

Fracalossi, D.M. et al., "Oscars, Astronotus ocellatus, have a dietary requirement for vitamin C," J. Nutrition (1998) 128:1745-1751.

Frei, B. et al., "Ubiquinol-10 is an effective lipid-soluble antioxidant at physiological concentrations," Proc. Natl. Acad. Sci. (1990) 87:4879-4883.

Gann, P.H. et al., "Lower prostate cancer risk in men with elevated plasma lycopene levels: results of a prospective analysis," Cancer Res. (1999) 59(6):1225-1230.

Gavin, P. et al., "Transdermal deliver yof various molecules in vivo using alpha-tocopheryl phosphate," Drug Delivery Today 2008) 8(9):34-41.

Ghayour-Mobarhan, M. et al., 'α-Tocopheryl Phosphate as a Bioactive Derivative of Vitamin E: A Review of the Literature', Journal of Dietary Supplements. 2014, vol. 12, No. 4, pp. 359-372.

Gianello, R. et al., "Subchronic oral toxicity study of mixed tocopheryl phosphates in rats," Int'l J. Toxicol. (2007) 26:475-490.

Gianello, R. et al., "α-tocopheryl phosphate: a novel, natural form of vitamin E," Free Radical Biol. Med. (2005) 39:970-976.

Godin, B. et al., "Ethosomes: new prospects in transdermal delivery," Crit. Rev. Thera. Drug Car. Syst. (2003) 20(1):63-102.

Goff et al., "Prevention of cardiovascular disease in persons with Type 2 diabetes mellitus: current knowledge and rationale for the action to control cardiovascular risk in diabetes (ACCORD) trial," Am. J. Cardiol. (2007) 99(suppl):4i-20i.

Griffin, E. et al., "A link between diabetes and atherosclerosis: glucose regulates expression of CD36 at the level of translation," Nature Med. (2001) 7(7):840-846.

Guo, J. et al., "Transdermal delivery of insulin in mice by using Lecithin vesicles as a carrier," Drug Del. (2000) 7:113-116.

Guthrie et al., "VIIth Asian Conference of Nutrition: Lipid Symposium Proceedings," Journal of Nutrition, 1997, vol. 127, pp. 544s-548s.

Heinrichs, J., "Mastitis prevention: the nutritional approach," Feed Mix, 2008, vol. 16, No. 6, 3 pages.

Heron-Milhavet, L. et al., "Muscle-specific overexpression of CD36 reverses the insulin resistance and diabetes of MKR mice," Endocrinology (2004) 145:4667-4676.

Iimura, N. et al., "Complex formation between cationic surfactantsand insoluble drugs," Bull. Chem. Soc. Jpn. (1999) 72:2417-2422.

Imada, I. et al., "Photochemical Reaction of Ubiquinone. IV. Coenzymatic activity of ubiquinone and related compounds," Chem. Pharm. Bull. (1965) 13:136-142.

International Specialty Products, "A Product Guide. Performance enhancing Products for Pharmaceuticals," (2005) 20 pages [retrieved on Jul. 27, 2010 from http://web.archieve.org/web/20060623233652/http://abstracts.aapspharmaceutica.com/ExpoAAPS06/Data/EC/Event/Exhibitors/309/4ecb9a3a-65d0-4c69-a762-c60e099922ee.pdf, published on Jun. 23, 2006 as per Wayback Machine].

Isoda, K. et al., "Metformin inhibits proinflammatory responses and nuclear factor-κB in human vascular wall cells," Arterioscler. Thromb. Vasc. Biol. (2006) 26:611-617.

Jiang, Q. et al., "γ-tocopherol induces apoptosis in androgen-responsive LNCaP prostate cancer cells via caspase-dependent and independent mechanisms," Annals of the New York Academy of Sciences, 2004, vol. 103, pp. 399-400.

Jiang, Q. et al., "γ-tocopherol, the major form of vitamin E in the U.S. diet, deserves more attention," Am. J. Clin. Nutri. (2001) 74(6):714-722.

Kagan, V. et al., "Antioxidant effects of ubiquinones in microsomes and mitochondria are mediated by tocopherol recycling," Biochem. Biophys. Res. Commun. (1990) 169(3):851-857.

Karrer, V.P. et al., "d,l-alpha-tocopherol-phosphorsaure-ester," Zurich, Chemisches Institut der Universitat (1933) p. 1137-1138, in German.

King, M.J. et al., "Transdermal delivery of insulin from a novel biphasic lipid system in diabetic rats," Diab. Tech. Therap. (2002) 4(4):479-488.

Knowler, W.C. et al., "Preventing Non-insulin-dependent diabetes," Diabetes (1995) 44:483-488.

Koh, "Antioxidants in a carotenoid-rich edible oil," Journal of Japan Mibyou System Association, 2003, vol. 9, No. 1, pp. 12-13.

Langsjoen, P.H. et al., "Overview of the use of CoQ10 in cardiovascular diseases," Biofactors (1999) 9:273-284.

Lass, A. et al., "Electron transport-linked ubiquinone-dependent recycling of α-tocopherol inhibits autooxidation of mitochondrial membranes," Arch. Biochem. Biophys. (1998) 352(2):229-236.

Lee, C-F. et al., "Attenuation of UV-induced apoptosis by coenzyme Q10 in human cells harboring large-scale deltion of mitochontrial DNA," Ann. N.Y. Acad. Sci. (2005) 1042:429-438.

Lei, B. et al., "Research progress in technique of preparing alpha-tocopherol," Xiandai Huagong (1997) 17(7):13-15.

(56) References Cited

OTHER PUBLICATIONS

Leira et al., "Irritant cutaneous reactions to N-methyl-2-pyrrolidone (NMP)" Contact Dermatitis, 1992; 27:148-150.
Li et al., "Effect of HPMC and Carbopol on the release and floating properties of gastric floating drug delivery system using factorial design." International Journal of Pharmaceutics, 2003; 253:13-22.
Libinaki, R. et al., "Evaluation of the safety of mixed tocopheryl phosphates (MTP)-a formulation of α-tocopheryl phosphate plus α-di-tocopheryl phosphate," Food Chem. Toxicol. (2006) 44(7):916-932.
Little, P.J. et al., "Phosphorylated troglitazone activates PPARγ and inhibits vascular smooth muscle cell proliferation and proteoglycan synthesis," J. Cardiovasc. Pharmacol. (2008) 51(3):274-279.
Madhavi et al., "Enhanced transdermal drug penetration of curcumin via ethosomes," Malaysian Journal of Pharmaceutical Sciences (2013) 11(1):49-58.
Magnusson et al., "Terpenes and ethanol enhance the transdermal permeation of the tripeptide thyrotropin releasing hormone in human epidermis," International Journal of Pharmaceutics 157, 1997, 113-121.
Maguire, J.J. et al., "Succinate-ubiquinone reductase linked recycling of alpha-tocopherol in reconstituted systems and mitochondria: requirement for reduced ubiquinone," Arch. Biochem. Biophys. (1992) 292(1):47-53.
Maugard et al., "Synthesis of Water-Soluble Retinol Derivatives by Enzymatic Method," Biotechnol. Prog., 2002, vol. 18, pp. 424-428.
Mellors, A. et al., "The inhibition of mitochondrial peroxidation by ubiquinone and ubiquinol," J. Biol. Chem. (1966) 241(19):4353-4356.
Merck Index, The, "Fludarabine to Fludeoxyglucose F18" pages, Thirteenth Edition, Whitehouse Station, NJ (2001) pp. 729-730.
Merck Index, The, "α-estradiol" Thirteenth Edition, Whitehouse Station, NJ (2001) p. 660.
Min, J. et al., "Effect of apoptosis induced by different vitamin E homologous analogues in human hepatoma cells (HepG2)," J. Hygiene Res. China (2003) 32(4):343-345.
Miyamoto, S. et al., "Synthesis of a novel phosphate ester of a vitamin E derivative and its antioxidative activity," Biosci. Biotech. Biochem. (1998) 62(12):2463-2466.
Morgan, T.M. et al., "Transdermal delivery of estradiol in postmenopausal women with a novel topical aerosol," J. Pharm. Sci. (1998) 87(10):1226-1228.
Morgan, T.M. et al., "Enhanced transdermal delivery of sex hormones in swine with a novel topical aerosol," J. Pharm. Sci. (1998) 87(10):1219-1225.
Mortensen, S.A., "Perspectives on therapy of cardiovascular diseases with coenzyme Q10 (ubiquinone)," Clin. Investig. (1993) 71(Suppl.8):S116-S123.
Mottu, F. et al., "Organic solvents for pharmaceutical parenterals and embolic liquids: a review of toxicity data," PDA Journal of Pharm. Sci. Tech. (2000) 54(6):456-469.
Mukherjee, S. et al., "Cardioprotection with a-tocopheryl phosphate: amelioration of myocardial ischemia reperfusion injury is linked with its ability to generate a survival signal through Akt activation," Biochim. Biophys. Acta (2008) 1782:498-503.
Munteanu, A. et al., "Modulation of cell proliferation and gene expression by alpha-tocopheryl phosphates: relevance to atherosclerosis and inflammation," Biochem. Biophys. Res. Comm. (2004) 318(1):311-316.
Nakayama, S. et al., "Protective effects of a stable, water-soluble vitamin E on photodamage induced by UVB irradiation in cultured mouse skin," Photomedicine and Photobiology (1998) 20:99-100.
Negis, Y. et al., "Molecular mechanism of alpha-tocopherylphospate transport across the cell membrane," Biochem. Biophys. Res. Comm. (2007) 359:348-353.
Negis, Y. et al., "On the existence of cellular tocopheryl phosphate, its synthesis, degradation and cellular roles: a hypothesis," IUBMB Life (2005) 57(1):23-25.

Negis, Y. et al., "The effect of tocopheryl phosphates on atherosclerosis progression in rabbits fed with a high cholesterol diet," Arch. Biochem. Biophys. (2006) 450:63-66.
Octoplus, "Formulation Development of Poorly Soluble Drugs" (www.octoplus.nl) (1999) 2 pages (downloaded Nov. 2008).
Ogru, E. et al., "Vitamin E phosphate: an endogenous form of vitamin E," Medimond S.r.l. (2003) 127-132.
Ostrenga, J. et al., "Significance of vehicle composition I: Relationship between topical vehicle composition, skin penetrability, and clinical efficacy," J. Pharm. Sci. (1971) 60(8):1175-1179.
Owens, D.R. et al., "Alternative routes of insulin delivery," Diabet. Med. (2003) 20:886-898.
Parker et al., "Neonatal vitamin K administration and childhood cancer in the North of England: retrospective case-control study," BMJ (1998) 316:189-193.
Pastori et al., "Lycopene in association with α-tocopherol inhibits at physiological concentrations proliferation of prostate carcinoma cells," Biochemical and Biophysical Research Communications, 1998, vol. 250, pp. 582-585.
Potts, R.O. et al., "Predicting skin permeability," Pharm. Res. (1992) 9(5):663-669.
Puratchikody, A. et al., "Reverse phase—high performance liquid chromatographic determination of atorvastatin calcium in solid dosage forms," Pharma. Review (2003) 1(2):79-80, 83—STN File CA, Abstract 139:399976 only.
Reference.com, "What are normal pH levels for the human stomach?" 2016, 1-5. Downloaded Nov. 8, 2016. <https:www.reference.com/science/normal-ph-levels-human-stomach-52a8c1518ee846ba>.
Rerek, M.E. et al., "Disodium lauriminodipropionate tocopheryl phosphates: a potent new antiinflammatory," Cosmetics & Toiletries magazine (2003) 118(7):63-67.
Rezk, B.M. et al., "The extraordinary antioxidant activity of vitamin E phosphate," Biochim. Biophys. Acta (2004) 1683:16-21.
Ricciarelli, R. et al., "Vitamin E reduces the uptake of oxidized LDL by inhibiting CD36 scavenger receptor expression in cultured aortic smooth muscle cells," Circulation (2000) 102:82-87.
Rosenson et al., "Hypertriglyceridemia is associated with an elevated blood viscosity Rosenson: triglycerides and blood viscosity", Atherosclerosis, 2002, vol. 161, Issue 2, pp. 433-439.
Saikinnno (1991) 149-155, 195-198.
Saishinn (1984) 137-147, 190-201.
Sanghvi et al., "Solubility Improvement of Drug using N-Methyl Pyrrolidone," AAPS Pharm Sci Tech, 2008, vol. 9, No. 2, pp. 366-376.
Schwenke, D.C. et al., "α-tocopherol protects against diet induced atherosclerosis in New Zealand white rabbits," J. Lipid Res. (2002) 43:1927-1938.
Sevast'ianov, V.I. et al., "Transdermal delivery of insulin," Meditsinskaia Tekhnika (2003) 2:21-24.
Seyama, Y. et al., "Comparative effects of Vitamin K2 and estradiol on experiemental arteriosclerosis with diabetes mellitus," Int. J. Vitam. Nutr. Res. (2000) 70(6):301-304, Abstract only.
Sharma H. et al., "An excerpt from the medical textbook Contemporary Ayurverda," Edinburgh: Churchill Livingston, 1998, 6 pages, Retrieved from Internet on Nov. 1, 2012 <http://www.bsherman.net/freeradicals.htm>.
Singh, R.B. et al., "Randomized double-blind placebo-controlled trial of coenzyme Q10 in patients with acute myocardial infarction," Cardiov. Drugs Ther. (1998) 12:347-353.
Sinha, V.R. et al., "Coating polymers for colon specific drug delivery: A comparative in vitro evaluation," Acta. Pharm., 2003, vol. 53, pp. 41-47.
Spears, J.W. et al., "Role of antioxidants and trace elements in health and immunity of transition dairy cows," The Veterinary Journal, 2008, 176:70-76.
Squillante et al., European Journal of Pharmaceutics and Biopharmaceutics 46 (1998) 265-271.
Stedman's Medical Dictionary, "Tocopherol," "Tocotrienol," and "Vitamin K1", 22nd Edition, Williams & Wilkins Co. (1972) p. 1303 and 1400.

(56) References Cited

OTHER PUBLICATIONS

Suzuki, T. et al., "The solution behavior and the association structure of long-chain monoalkyl phosphates," Chem. Soc. Japan (1986) 633-640, with English abstract.
Teupser, D. et al., "Alpha-tocopherol down-regulates scavenger receptor activity in macrophages," Atherosclerosis (1999) 144:109-115.
Traber, M.G. et al., "Human plasma vitamin E kinetics demonstrates rapid recycling of plasma RRR-alpha-tocophero," Proc. Natl. Acad. Sci. USA (1994) 91:10005-10008.
Trommer et al., "Overcoming the Stratum Corneum: The Modulation of Skin Penetration," Skin Pharmacol Physiol, 2006, 19:106-121.
Visarius, T. et al., "Inhibition of human prostate cancer cell proliferation: vitamin E and lycopene targeted pathways regulating cell cycle progression," FASEB J. (2004) 18(8):C103.
Walters et al., "The effects of surfactants on penetration across the skin," Inter. J. Cosmetic Sci. (1993) 15:260-270.
Williams, A.C. et al., "Penetration enhancers," Advanced Drug Delivery Reviews (2004) 56(5):603-618.
Younis et al., "The prevention of type 2 diabetes mellitus: recent advances," Q.J. Med. (2004) 97:451-455.
Zia et al., "Cosolvency of Dimethyl Isosorbide for Steroid Solubility," Pharmaceutical Research, 1991, 8(4):502-504.
Zingg, J.-M. et al., "α-Tocopheryl phosphate—An active lipid mediator?", Molecular Nutrition and Food Research. 2010, vol. 54, pp. 679-692.
English Machine Translation of CN101524330A, published Sep. 9, 2009.
United States Office Action for U.S. Appl. No. 09/979,436 dated Apr. 4, 2002 (6 pages).
United States Office Action for U.S. Appl. No. 09/979,436 dated Sep. 23, 2002 (6 pages).
United States Office Action for U.S. Appl. No. 10/416,775 dated Nov. 2, 2005 (10 pages).
United States Office Action for U.S. Appl. No. 10/416,775 dated Jun. 12, 2006 (10 pages).
United States Office Action for U.S. Appl. No. 10/416,775 dated Jul. 12, 2007 (11 pages).
United States Office Action for U.S. Appl. No. 10/416,775 dated Dec. 17, 2008 (6 pages).
United States Patent Office Action for U.S. Appl. No. 12/628,443 dated Feb. 18, 2011 (15 pages).
United States Patent Office Action for U.S. Appl. No. 12/628,443 dated Aug. 5, 2011 (8 pages).
United States Patent Office Notice of Allowance for U.S. Appl. No. 12/628,443 dated Jan. 12, 2012 (7 pages).
United States Office Action for U.S. Appl. No. 10/416,774 dated Sep. 6, 2007 (9 pages).
United States Office Action for U.S. Appl. No. 10/416,774 dated Jun. 11, 2008 (15 pages).
United States Office Action for U.S. Appl. No. 10/416,774 dated Feb. 17, 2009 (15 pages).
United States Office Action for U.S. Appl. No. 10/416,774 dated Apr. 15, 2009 (14 pages).
United States Patent Office Action for U.S. Appl. No. 10/416,774 dated Dec. 18, 2009 (11 pages).
United States Office Action for U.S. Appl. No. 10/462,480 dated Dec. 1, 2006 (10 pages).
United States Office Action for U.S. Appl. No. 10/462,480 dated Nov. 1, 2007 (10 pages).
United States Office Action for U.S. Appl. No. 10/462,480 dated Feb. 20, 2009 (17 pages).
United States Patent Office Action for U.S. Appl. No. 10/462,480 dated Nov. 27, 2009 (9 pages).
United States Patent Office Action for U.S. Appl. No. 12/768,307 dated Oct. 6, 2011 (13 pages).
United States Patent Office Action for U.S. Appl. No. 12/782,438 dated Aug. 30, 2012 (14 pages).
United States Office Action for U.S. Appl. No. 10/485,196 dated May 29, 2008 (23 pages).
United States Office Action for U.S. Appl. No. 10/485,196 dated Jul. 23, 2009 (9 pages).
United States Patent Office Action for U.S. Appl. No. 10/485,196 dated Jan. 25, 2010 (8 pages).
United States Patent Office Action for U.S. Appl. No. 10/485,196 dated Oct. 29, 2010 (13 pages).
United States Patent Office Notice of Allowance for U.S. Appl. No. 10/485,196 dated Apr. 14, 2011 (7 pages).
United States Office Action for U.S. Appl. No. 10/486,142 dated Mar. 18, 2008 (12 pages).
United States Patent Office Action for U.S. Appl. No. 12/212,803 dated Mar. 12, 2010 (13 pages).
United States Office Action for U.S. Appl. No. 10/487,743 dated Dec. 2, 2005 (22 pages).
United States Office Action for U.S. Appl. No. 10/487,743 dated Jul. 27, 2006 (23 pages).
United States Office Action for U.S. Appl. No. 10/498,684 dated Oct. 2, 2008 (21 pages).
United States Office Action for U.S. Appl. No. 10/498,684 dated Jun. 23, 2009 (19 pages).
United States Patent Office Action for U.S. Appl. No. 10/498,684 dated Jul. 7, 2010 (21 pages).
United States Office Action for U.S. Appl. No. 10/524,090 dated Mar. 12, 2008 (12 pages).
United States Patent Office Action for U.S. Appl. No. 10/524,090 dated Mar. 3, 2010 (18 pages).
United States Patent Office Action for U.S. Appl. No. 10/524,090 dated Nov. 23, 2010 (19 pages).
United States Office Action for U.S. Appl. No. 10/542,511 dated Aug. 8, 2007 (19 pages).
United States Office Action for U.S. Appl. No. 10/542,511 dated Mar. 31, 2008 (20 pages).
United States Office Action for U.S. Appl. No. 10/542,511 dated Feb. 5, 2009 (23 pages).
United States Patent Office Action for U.S. Appl. No. 10/542,511 dated Jan. 12, 2010 (13 pages).
United States Patent Office Advisory Action for U.S. Appl. No. 10/542,511 dated May 25, 2010 (3 pages).
United States Patent Office Action for U.S. Appl. No. 12/834,553 dated Apr. 14, 2011 (13 pages).
United States Patent Office Action for U.S. Appl. No. 12/834,553 dated Oct. 7, 2011 (11 pages).
United States Office Action for U.S. Appl. No. 10/551,200 dated Jan. 28, 2009 (11 pages).
United States Office Action for U.S. Appl. No. 10/551,201 dated Jan. 24, 2008 (6 pages).
United States Office Action for U.S. Appl. No. 10/551,203 dated Dec. 6, 2006 (13 pages).
United States Office Action for U.S. Appl. No. 10/551,203 dated Sep. 7, 2007 (13 pages).
United States Office Action for U.S. Appl. No. 10/551,203 dated Apr. 11, 2008 (11 pages).
United States Office Action for U.S. Appl. No. 10/551,203 dated Dec. 19, 2008 (13 pages).
United States Office Action for U.S. Appl. No. 10/551,203 dated Jul. 21, 2009 (21 pages).
United States Patent Office Action for U.S. Appl. No. 12/690,735 dated Sep. 27, 2011 (15 pages).
United States Patent Office Action for U.S. Appl. No. 12/690,735 dated Aug. 2, 2012 (9 pages).
United States Patent Office Action for U.S. Appl. No. 11/572,864 dated Mar. 15, 2012 (15 pages).
United States Patent Office Action for U.S. Appl. No. 11/572,864 dated Nov. 8, 2012 (16 pages).
United States Patent Office Action for U.S. Appl. No. 11/572,864 dated Sep. 16, 2013 (10 pages).
United States Patent Office Action for U.S. Appl. No. 11/572,864 dated Jun. 20, 2014 (11 pages).
United States Patent Office Action for U.S. Appl. No. 11/817,439 dated Nov. 24, 2010 (15 pages).

(56) References Cited

OTHER PUBLICATIONS

United States Patent Office Action for U.S. Appl. No. 11/817,439 dated May 11, 2011 (11 pages).
United States Patent Office Action for U.S. Appl. No. 11/817,439 dated Jul. 29, 2011 (2 pages).
United States Patent Office Action for U.S. Appl. No. 11/817,439 dated Nov. 7, 2012 (10 pages).
United States Patent Office Action for U.S. Appl. No. 11/817,453 dated Oct. 9, 2009 (11 pages).
United States Patent Office Action for U.S. Appl. No. 11/817,453 dated Aug. 2, 2010 (10 pages).
United States Patent Office Action for U.S. Appl. No. 11/817,453 dated Mar. 9, 2011 (12 pages).
United States Patent Office Action for U.S. Appl. No. 11/817,453 dated Oct. 13, 2011 (14 pages).
United States Patent Office Action for U.S. Appl. No. 11/817,453 dated Feb. 21, 2014 (13 pages).
United States Patent Office Action for U.S. Appl. No. 11/917,831 dated Jan. 19, 2011 (10 pages).
United States Patent Office Action for U.S. Appl. No. 11/917,831 dated Oct. 24, 2011 (11 pages).
United States Patent Office Action for U.S. Appl. No. 11/917,831 dated Oct. 3, 2014 (9 pages).
United States Patent Office Notice of Allowance for U.S. Appl. No. 11/917,831 dated Jul. 8, 2015 (7 pages).
United States Patent Office Action for U.S. Appl. No. 12/158,932 dated Aug. 19, 2010 (15 pages).
United States Patent Office Action for U.S. Appl. No. 13/501,494 dated Dec. 18, 2012 (13 pages).
United States Patent Office Final Rejection for U.S. Appl. No. 13/501,494 dated Aug. 22, 2013 (13 pages).
United States Patent Office Action for U.S. Appl. No. 13/501,494 dated Apr. 21, 2014 (19 pages).
United States Patent Office Action for U.S. Appl. No. 13/501,494 dated Nov. 18, 2014 (16 pages).
United States Patent Office Action for U.S. Appl. No. 13/501,494 dated Jan. 26, 2016 (20 pages).
United States Patent Office Action for U.S. Appl. No. 15/218,719 dated Sep. 25, 2017 (12 pages).
United States Patent Office Action for U.S. Appl. No. 13/501,498 dated Feb. 21, 2013 (12 pages).
United States Patent Office Final Rejection for U.S. Appl. No. 13/501,498 dated Nov. 14, 2013 (10 pages).
United States Patent Office Action for U.S. Appl. No. 13/501,498 dated Nov. 21, 2014 (9 pages).
United States Patent Office Final Rejection for U.S. Appl. No. 13/501,498 dated Apr. 8, 2015 (16 pages).
United States Patent Office Action for U.S. Appl. No. 13/501,498 dated Dec. 4, 2015 (10 pages).
United States Patent Office Action for U.S. Appl. No. 13/501,498 dated Jun. 9, 2016 (14 pages).
United States Patent Office Action for U.S. Appl. No. 15/261,455 dated Feb. 27, 2017 (12 pages).
United States Patent Office Action for U.S. Appl. No. 15/261,455 dated Sep. 6, 2017 (10 pages).
United States Patent Office Action for U.S. Appl. No. 15/261,455 dated Mar. 22, 2018 (6 pages).
United States Patent Office Action for U.S. Appl. No. 15/261,455 dated Dec. 11, 2018 (20 pages).
United States Patent Office Action for U.S. Appl. No. 16/438,245 dated Nov. 29, 2019 (9 pages).
United States Patent Office Action for U.S. Appl. No. 12/782,560 dated Sep. 1, 2011 (18 pages).
United States Patent Office Action for U.S. Appl. No. 12/782,560 dated May 24, 2012 (22 pages).
United States Patent Office Action for U.S. Appl. No. 13/501,499 dated Sep. 25, 2013 (12 pages).
United States Patent Office Action for U.S. Appl. No. 13/683,698 dated Apr. 24, 2013 (18 pages).
United States Patent Office Final Rejection for U.S. Appl. No. 13/683,698 dated Nov. 14, 2013 (15 pages).
United States Patent Office Action for U.S. Appl. No. 13/683,698 dated Jun. 20, 2014 (17 pages).
United States Patent Office Final Rejection for U.S. Appl. No. 13/683,698 dated Jan. 29, 2015 (17 pages).
United States Patent Office Action for U.S. Appl. No. 13/683,698 dated Sep. 1, 2015 (19 pages).
United States Patent Office Action for U.S. Appl. No. 12/782,564 dated Sep. 1, 2011 (20 pages).
United States Patent Office Action for U.S. Appl. No. 12/782,564 dated May 24, 2012 (25 pages).
United States Patent Office Action for U.S. Appl. No. 13/501,500 dated Dec. 17, 2012 (14 pages).
United States Patent Office Notice of Allowance for U.S. Appl. No. 13/501,500 dated Aug. 21, 2013 (11 pages).
United States Patent Office Action for U.S. Appl. No. 14/086,738 dated May 22, 2014 (14 pages).
United States Patent Office Action for U.S. Appl. No. 14/550,514 dated Apr. 23, 2015 (13 pages).
United States Patent Office Notice of Allowance for U.S. Appl. No. 14/550,514 dated Dec. 10, 2015 (6 pages).
United States Patent Office Action for U.S. Appl. No. 15/065,510 dated Dec. 12, 2016 (14 pages).
United States Patent Office Action for U.S. Appl. No. 13/577,124 dated Feb. 14, 2013 (15 pages).
United States Patent Office Final Rejection for U.S. Appl. No. 13/577,124 dated Aug. 2, 2013 (14 pages).
United States Patent Office Action for U.S. Appl. No. 13/577,124 dated Dec. 26, 2014 (9 pages).
United States Patent Office Final Rejection for U.S. Appl. No. 13/577,124 dated Jul. 22, 2015 (11 pages).
United States Patent Office Action for U.S. Appl. No. 13/577,124 dated Jun. 16, 2016 (8 pages).
United States Patent Office Final Rejection for U.S. Appl. No. 13/577,124 dated Nov. 15, 2016 (10 pages).
United States Patent Office Action for U.S. Appl. No. 14/004,973 dated Apr. 9, 2015 (12 pages).
United States Patent Office Final Rejection for U.S. Appl. No. 14/004,973 dated Oct. 20, 2015 (14 pages).
United States Patent Office Action for U.S. Appl. No. 14/004,973 dated Apr. 13, 2016 (13 pages).
United States Patent Office Notice of Allowance for U.S. Appl. No. 14/004,973 dated Sep. 28, 2016 (5 pages).
United States Patent Office Action for U.S. Appl. No. 15/400,356 dated Oct. 19, 2017 (12 pages).
United States Patent Office Action for U.S. Appl. No. 15/400,356 dated Feb. 22, 2018 (12 pages).
United States Patent Office Action for U.S. Appl. No. 16/060,868 dated May 14, 2019 (10 pages).
United States Patent Office Action for U.S. Appl. No. 16/060,868 dated Dec. 27, 2019 (15 pages).
United States Patent Office Action for U.S. Appl. No. 16/060,868 dated Jul. 22, 2020 (13 pages).
United States Patent Office Action for U.S. Appl. No. 16/467,759 dated Sep. 3, 2020 (11 pages).
United States Patent Notice of Allowance for U.S. Appl. No. 16/060,868 dated Nov. 25, 2020 (7 pages).
United States Patent Office Action for U.S. Appl. No. 16/470,943 dated Dec. 8, 2020 (6 pages).
United States Patent Office Action for U.S. Appl. No. 16/467,759 dated Dec. 21, 2020 (11 pages).
United States Patent Office Action for U.S. Appl. No. 16/470,943 dated Jun. 18, 2021 (6 pages).
International Search Report and Written Opinion for Application No. PCT/AU2010/001719 dated Mar. 8, 2011 (11 pages).
International Preliminary Report on Patentability for Application No. PCT/AU2010/001719 dated Nov. 11, 2011 (6 pages).
International Search Report and Written Opinion for Application No. PCT/AU2011/000122 dated Apr. 6, 2011 (14 pages).
Written Opinion for Application No. PCT/AU2011/000122 dated Jan. 3, 2012 (4 pages).

(56) References Cited

OTHER PUBLICATIONS

International Preliminary Report on Patentability for Application No. PCT/AU2011/000122 dated Mar. 13, 2012 (5 pages).
International Search Report and Written Opinion for Application No. PCT/AU2010/000580 dated Jun. 29, 2010 (8 pages).
International Preliminary Report on Patentability for Application No. PCT/AU2010/000580 dated Feb. 20, 2012 (5 pages).
International Search Report and Written Opinion for Application No. PCT/AU2011/000358 dated May 31, 2011 (10 pages).
Written Opinion for Application No. PCT/AU2011/000358 dated Feb. 21, 2012 (7 pages).
International Search Report and Written Opinion for Application No. PCT/AU2011/000112 dated Feb. 25, 2011 (8 pages).
International Preliminary Report on Patentability for Application No. PCT/AU2011/000112 dated Jun. 6, 2012 (15 pages).
International Search Report, PCT/AU2012/000220 dated Apr. 2, 2012 (3 pages).
Written Opinion for Application No. PCT/AU2012/000220 dated Apr. 2, 2012 (2 pages).
International Search Report for Application No. PCT/AU2016/051209 dated Feb. 2, 2017 (12 pages).
International Preliminary Report of Patentability for Application No. PCT/AU2016/051209 dated Mar. 22, 2018 (6 pages).
International Search Report for Application No. PCT/AU2017/051381, dated Feb. 13, 2018 (6 pages).
Written Opinion for Application No. PCT/AU2017/051381, dated Feb. 13, 2018 (6 pages).
International Preliminary Report On Patentability for Application No. PCT/AU2017/051381, dated Apr. 8, 2019 (39 pages).
International Search Report for Application No. PCT/AU2017/051363, dated Jan. 25, 2018 (6 pages).
Written Opinion for Application No. PCT/AU2017/051363, dated Jan. 25, 2018 (5 pages).
European Patent Office Extended Search Report for Application No. 17883017.0 dated Oct. 24, 2019 (8 pages).
Helvetica Chimica Acta—1963—Schudel—ber die Chemie des Vitamins E 1 Mitteilung Die Umkehrung der Konfiguration am.
United States Patent Office Action for U.S. Appl. No. 17/353,343 dated Oct. 12, 2022 (11 pages).
United States Patent Office Action for U.S. Appl. No. 17/353,343 dated Apr. 24, 2023 (10 pages).

PROCESS

CROSS-REFERENCE TO RELATED APPLICATIONS

This patent application is a continuation of U.S. patent application Ser. No. 16/470,943, filed Jun. 18, 2019, which is the national stage entry, under 35 U.S.C. § 371 of International Application Number PCT/AU2017/051381, filed Dec. 13, 2017, which claims priority to Australian Patent Application Number 2016905298, filed Dec. 21, 2016, the disclosures of which are incorporated by reference herein in their entireties. Priority to each application is hereby claimed.

TECHNICAL FIELD

The invention relates to a phosphorylation process of complex alcohols, and products obtained by that process.

BACKGROUND

It is to be understood that, if any prior art publication is referred to herein, such reference does not constitute an admission that the publication forms a part of the common general knowledge in the art, in Australia or any other country.

Phosphorylation processes and reagents are chosen to avoid significant degradation of the compound being phosphorylated and to produce desired yields.

In some phosphorylation processes, reagents such as 2:2:2-trichloroethyl dichlorophosphate, di-imidazolide chlorophosphate and di-analide chlorophosphate are used under gentle conditions to avoid degradation of the compound being phosphorylated. However, such processes have been found to produce limited yields, which would not be economical or suitable for commercial purposes.

In other phosphorylation processes, the reagent phosphorous oxychloride is used, but the reaction typically produces a variety of by-products and hydrogen chloride. Such process may also not be commercially viable given that the reagent phosphorous oxychloride is difficult to handle.

The reagent $P_4O_{10}$, which is commonly known as phosphorus pentoxide, but has other names such as phosphorus (V) oxide, phosphoric anhydride and diphosphorus pentoxide, is a white crystalline solid. This reagent has been used for phosphorylation of ethanol and other short chain primary alcohols (i.e. less than 6 carbon atoms) and it has been found to be suitable for phosphorylation of alcohols such as primary fatty alcohols, secondary alcohols and aromatic alcohols. Australian Patent No. 200043870 describes a process, which involves forming an intimate mixture of one or more of these alcohols and $P_4O_{10}$, partly hydrated $P_4O_{10}$ or a mixture thereof, at a temperature below 80° C., and allowing the intimate mixture to continue to react for a period of time at this temperature, i.e. below 80° C., until formation of the phosphorylated alcohol is substantially formed. It is clear that the temperature must be kept to a minimum and below 80° C. to avoid degradation.

The phosphorylation of complex alcohols, such as secondary and tertiary alcohols, with $P_4O_{10}$ at higher temperatures was thought to lead to degradation and/or side reactions such as dehydration and double bond formation. These problems teach away from the use of $P_4O_{10}$ for the efficient and commercial phosphorylation of complex alcohols at high temperatures.

The present inventors have found that complex alcohols can be phosphorylated at a high temperature and that, at such temperatures, desirable yields can be obtained with minimal degradation of the complex alcohols.

SUMMARY

Accordingly, there is provided a process for phosphorylating a complex alcohol, comprising the steps of:
(a) mixing the complex alcohol and $P_4O_{10}$ until its exothermic reaction temperature is achieved;
(b) allowing the reaction mixture of step (a) to react until the exothermic reaction is complete, and heating the reaction mixture of step (a) to within a range of at least about 90° C. to 140° C., if required;
(c) cooling the reaction mixture of step (b) to at least about 80° C.; and
(d) hydrolysing the reaction mixture of step (c), wherein hydrolysis is conducted for about 30 to about 90 minutes.

There is also provided a product obtained by the process.

DETAILED DESCRIPTION

The invention relates to a process for phosphorylating a complex alcohol, comprising the steps of:
(a) mixing the complex alcohol and $P_4O_{10}$ until its exothermic reaction temperature is achieved;
(b) allowing the reaction mixture of step (a) to react until the exothermic reaction is complete, and heating the reaction mixture of step (a) to within a range of at least about 90° C. to 140° C., if required;
(c) cooling the reaction mixture of step (b) to at least about 80° C.; and
(d) hydrolysing the reaction mixture of step (c), wherein hydrolysis is conducted for about 30 to about 90 minutes.

Complex Alcohol

The complex alcohol may be a linear or branched alcohol comprising at least 6 carbon atoms (i.e. 6 or more carbon atoms). In some embodiments, the complex alcohol comprises at least 7 carbon atoms. In other embodiments, the complex alcohol comprises at least 8 carbon atoms. In particular embodiments, the complex alcohol comprises at least 10 carbon atoms. The number of carbon atoms mentioned herein refers to the number of carbon atoms that make up the backbone of the linear or branched complex alcohol or the ring system of the cyclic complex alcohol.

Examples of linear and branched complex alcohols include, but are not limited to, hexanol, hexan-1-ol, heptanol, heptan-1-ol, octanol, octan-1-ol, decanol, decan-1-ol, undecanol, dodecanol, 1-dodecanol, tridecanol, 1-tetradecanol, pentadecanol, cetyl alcohol, stearyl alcohol, 1-methylhexan-1-ol, 2-methylhexan-1-ol, 3-methyl-heptan-1-ol, 4-methylhexan-1-ol, 1-methylhexan-2-ol, 2-methylhexan-2-ol, 3-methyl-hexan-2-ol, 4-methylhexan-2-ol, 1-methylhexan-3-ol, 2-methylhexan-3-ol, 3-methyl-hexan-3-ol, 4-methylhexan-3-ol, 1-methylhexan-4-ol, 2-methylhexan-4-ol, 3-methyl-hexan-4-ol, 4-methylhexan-4-ol, 1-methylhexan-5-ol, 2-methylhexan-5-ol, 3-methyl-hexan-5-ol, 4-methylhexan-5-ol, 1-methylhexan-6-ol, 2-methylhexan-6-ol, 3-methyl-hexan-6-ol, 4-methylhexan-6-ol, 1-ethylhexan-1-ol, 2-ethylhexan-1-ol, 3-ethyl-hexan-1-ol, 4-methylhexan-1-ol, 1-ethylhexan-2-ol, 2-ethylhexan-2-ol, 3-ethyl-hexan-2-ol, 4-ethylhexan-2-ol, 1-ethylhexan-3-ol, 2-ethylhexan-3-ol, 3-ethyl-hexan-3-ol, 4-ethylhexan-3-ol, 1-ethylhexan-4-ol, 2-ethylhexan-4-ol, 3-ethyl-hexan-4-ol, 4-ethylhexan-4-ol, 1-ethylhexan-5-ol, 2-ethylhexan-5-ol, 3-ethyl-hexan-5-ol, 4-ethylhexan-5-ol, 1-ethylhexan-6-ol, 2-ethylhexan-6-ol, 3-ethyl-hexan-6-ol, 4-ethylhexan-6-ol, 1-methylheptan-1-ol, 2-methylheptan-1-ol, 3-methyl-heptan-1-ol, 4-methylheptan-1-ol, 1-methylheptan-2-ol, 2-methylheptan-2-ol, 3-methyl-heptan-2-ol, 4-methylheptan-2-ol, 1-methylheptan-3-ol, 2-methylheptan-3-ol, 3-methyl-heptan-3-ol, 4-methylheptan-3-ol, 1-methylheptan-4-ol, 2-methylheptan-4-ol, 3-methyl-heptan-4-ol, 4-methylheptan-4-ol, 1-methylheptan-5-ol, 2-methylheptan-5-ol, 3-methyl-heptan-5-ol, 4-methylheptan-5-ol, 1-methylheptan-6-ol, 2-methylheptan-6-ol, 3-methyl-heptan-6-ol, 4-methylheptan-6-ol, 1-methylheptan-7-ol, 2-methylheptan-7-ol, 3-methyl-heptan-7-ol, 4-methylheptan-7-ol-ethylheptan-1-ol, 2-ethylheptan-1-ol, 3-ethyl-heptan-1-ol, 4-methylheptan-1-ol, 1-ethylheptan-2-ol, 2-ethylheptan-2-ol, 3-ethyl-heptan-2-ol, 4-ethylheptan-2-ol, 1-ethylheptan-3-ol, 2-ethylheptan-3-ol, 3-ethyl-heptan-3-ol, 4-ethylheptan-3-ol, 1-ethylheptan-4-ol, 2-ethylheptan-4-ol, 3-ethyl-heptan-4-ol, 4-ethylheptan-4-ol, 1-ethylheptan-5-ol, 2-ethylheptan-5-ol, 3-ethyl-heptan-5-ol, 4-ethylheptan-5-ol, 1-ethylheptan-6-ol, 2-ethylheptan-6-ol, 3-ethyl-heptan-6-ol, 4-ethylheptan-6-ol, 1-ethylheptan-7-ol, 2-ethylheptan-7-ol, 3-ethyl-heptan-7-ol, 4-ethylheptan-7-ol, 1-methyloctan-1-ol, 2-methyloctan-1-ol, 3-methyl-octan-1-ol, 4-methyloctan-1-ol, 1-methyloctan-2-ol, 2-methyloctan-2-ol, 3-methyl-octan-2-ol, 4-methyloctan-2-ol, 1-methyloctan-3-ol, 2-methyloctan-3-ol, 3-methyl-octan-3-ol, 4-methyloctan-3-ol, 1-methyloctan-4-ol, 2-methyloctan-4-ol, 3-methyl-octan-4-ol, 4-methyloctan-4-ol, 1-methyloctan-5-ol, 2-methyloctan-5-ol, 3-methyl-octan-5-ol, 4-methyloctan-5-ol, 1-methyloctan-6-ol, 2-methyloctan-6-ol, 3-methyl-octan-6-ol, 4-methyloctan-6-ol, 1-methyloctan-7-ol, 2-methyloctan-7-ol, 3-methyl-octan-7-ol, 4-methyloctan-7-ol, 1-methyloctan-8-ol, 2-methyloctan-8-ol, 3-methyl-octan-8-ol, 4-methyloctan-8-ol,1-ethyloctan-1-ol, 2-ethyloctan-1-ol, 3-ethyl-octan-1-ol, 4-methyloctan-1-ol, 1-ethyloctan-2-ol, 2-ethyloctan-2-ol, 3-ethyl-octan-2-ol, 4-ethyloctan-2-ol, 1-ethyloctan-3-ol, 2-ethyloctan-3-ol, 3-ethyl-octan-3-ol, 4-ethyloctan-3-ol, 1-ethyloctan-4-ol, 2-ethyloctan-4-ol, 3-ethyl-octan-4-ol, 4-ethyloctan-4-ol, 1-ethyloctan-5-ol, 2-ethyloctan-5-ol, 3-ethyl-octan-5-ol, 4-ethyloctan-5-ol, 1-ethyloctan-6-ol, 2-ethyloctan-6-ol, 3-ethyl-octan-6-ol, 4-ethyloctan-6-ol, 1-ethyloctan-7-ol, 2-ethyloctan-7-ol, 3-ethyl-octan-7-ol, 4-ethyloctan-7-ol, 1-ethyloctan-8-ol, 2-ethyloctan-8-ol, 3-ethyl-octan-8-ol, 4-ethyloctan-8-ol, 1-methylnonan-1-ol, 2-methylnonan-1-ol, 3-methyl-nonan-1-ol, 4-methylnonan-1-ol, 1-methyl-nonan-2-ol, 2-methylnonan-2-ol, 3-methyl-nonan-2-ol, 4-methylnonan-2-ol, 1-methylnonan-3-ol, 2-methylnonan-3-ol, 3-methyl-nonan-3-ol, 4-methylnonan-3-ol, 1-methylnonan-4-ol, 2-methylnonan-4-ol, 3-methyl-nonan-4-ol, 4-methylnonan-4-ol, 1-methylnonan-5-ol, 2-methylnonan-5-ol, 3-methyl-nonan-5-ol, 4-methylnonan-5-ol, 1-methylnonan-6-ol, 2-methylnonan-6-ol, 3-methyl-nonan-6-ol, 4-methylnonan-6-ol, 1-methylnonan-7-ol, 2-methylnonan-7-ol, 3-methyl-nonan-7-ol, 4-methylnonan-7-ol, 1-methylnonan-8-ol, 2-methylnonan-8-ol, 3-methyl-nonan-8-ol, 4-methylnonan-8-ol, 1-methylnonan-9-ol, 2-methylnonan-9-ol, 3-methyl-nonan-9-ol, 4-methylnonan-9-ol, 1-ethylnonan-1-ol, 2-ethylnonan-1-ol, 3-ethyl-nonan-1-ol, 4-methylnonan-1-ol, 1-ethylnonan-2-ol, 2-ethylnonan-2-ol, 3-ethyl-nonan-2-ol, 4-ethylnonan-2-ol, 1-ethylnonan-3-ol, 2-ethylnonan-3-ol, 3-ethyl-nonan-3-ol, 4-ethylnonan-3-ol, 1-ethylnonan-4-ol, 2-ethylnonan-4-ol, 3-ethyl-nonan-4-ol, 4-ethylnonan-4-ol, 1-ethylnonan-5-ol, 2-ethylnonan-5-ol, 3-ethyl-nonan-5-ol, 4-ethylnonan-5-ol, 1-ethylnonan-6-ol, 2-ethylnonan-6-ol, 3-ethyl-nonan-6-ol, 4-ethylnonan-6-ol, 1-ethylnonan-7-ol, 2-ethylnonan-7-ol, 3-ethyl-nonan-7-ol, 4-ethylnonan-7-ol, 1-ethylnonan-8-ol, 2-ethylnonan-8-ol, 3-ethyl-nonan-8-ol, 4-ethylnonan-8-ol, 1-ethylnonan-9-ol, 2-ethylnonan-9-ol, 3-ethyl-nonan-9-ol, and 4-ethylnonan-9-ol.

The complex alcohol may be a cyclic complex alcohol and may be carbocyclic or heterocyclic. Further, the carbocyclic or heterocyclic complex alcohol may be aromatic or non-aromatic. In some embodiments, the heterocyclic complex alcohol comprises one or more heteroatoms. In one embodiment, the heterocyclic complex alcohol comprises one heteroatom. In another embodiment, the heterocyclic complex alcohol comprises two heteroatoms. The heteroatom may be selected from the group consisting of N, O, S and P.

The cyclic complex alcohol may also be monocyclic or polycyclic. The polycyclic complex alcohol may comprise 2 or more rings. In some embodiments, the polycyclic complex alcohol comprises 2 or more rings, wherein at least 2 rings are fused.

In particular embodiments, the complex alcohol is a sterol. The sterol may be a phytosterol. In one specific embodiment, the sterol is cholesterol.

In other particular embodiments, the complex alcohol is a chromanol. In some embodiments, the chromanol is a tocopherol or tocotrienol.

In some embodiments, the tocopherol is natural, synthetic, or a combination thereof. Natural tocopherol typically comprises about 96% a-tocopherol and a small amount of γ-tocopherol. Synthetic tocopherol, on the other hand, typically comprises about 99-98% α-tocopherol. Furthermore, synthetic tocopherol comprises a mixture of the 8 possible stereoisomers, where only 1 occurs naturally.

In other embodiments, the tocopherol is α-tocopherol, β-tocopherol, γ-tocopherol, δ-tocopherol, or a combination thereof. In particular embodiments, the tocopherol comprises α-tocopherol. In one embodiment, the tocopherol comprises equal to or greater than about 90% α-tocopherol. In another embodiment, the tocopherol is a-tocopherol (i.e. 100% α-tocopherol).

The complex alcohol may also be a pharmaceutical compound, an anaesthetic, or an antioxidant.

In some embodiments, the pharmaceutical compound is an oncology drug such as a taxane, a nucleoside or a kinase inhibitor, a steroid, an opioid analgesic, a respiratory drug, a central nervous system (CNS) drug, a hypercholesterolemia drug, an antihypertensive drug, an immunosuppressive drug, an antibiotic, a luteinising hormone releasing hormone (LHRH) agonist, a LHRH antagonist, an antiviral drug, an antiretroviral drug, an estrogen receptor modulator, a somatostatin mimic, an anti-inflammatory drug, a vitamin $D_2$ analogue, a synthetic thyroxine, an antihistamine, an antifungal agent, a nonsteroidal anti-inflammatory drug (NSAID) or an anesthetic.

Suitable oncology drugs include taxanes such as paclitaxel, cabazitaxel and docetaxel, camptothecin and its analogues such as irinotecan and topotecan, other antimicrotubule agents such as vinflunine, nucleosides such as gemcitabine, cladribine, fludarabine capecitabine, decitabine, azacitidine, clofarabine and nelarabine, kinase inhibitors such as sprycel, temisirolimus, dasatinib, AZD6244, AZD1152, PI-103, R-roscovitine, olomoucine and purvalanol A, and epothilone B analogues such as ixabepilone, anthrocyclines such as amrubicin, doxorubicin, epirubicin and valrubicin, super oxide inducers such as trabectecin, proteosome inhibitors such as bortezomib and other topoisomerase inhibitors, intercalating agents and alkylating agents.

Suitable steroids include anabolic steroids such as testosterone, dihydrotestosterone, estradiol and ethynylestradiol, and corticosteroids such as cortisone, prednisilone, budesonide, triamcinolone, fluticasone, mometasone, amcinonide, flucinolone, fluocinanide, desonide, halcinonide, prednicarbate, fluocortolone, dexamethasone, betamethasone and fluprednidine.

Suitable opioid analgesics include morphine, oxymorphone, naloxone, codeine, oxycodone, methylnaltrexone, hydromorphone, buprenorphine and etorphine.

Suitable respiratory drugs include bronchodilators, inhaled steroids, and decongestants and more particularly salbutamol, ipratropium bromide, montelukast and formoterol. Suitable CNS drugs include antipsychotic such as quetiapine and antidepressants such as venlafaxine.

Suitable drugs to control hypercholesterolemia include ezetimibe and statins such as simvastatin, lovastatin, atorvastatin, fluvastatin, pitavastatin, pravastatin and rosuvastatin.

Suitable antihypertensive drugs include losartan, olmesartan, medoxomil, metrolol, travoprost and bosentan.

Suitable immunosuppressive drugs include glucocorticoids, cytostatics, antibody fragments, anti-immunophilins, interferons, TNF binding proteins and more particularly cacineurin inhibitors such as tacrolimus, mycophenolic acid and its derivatives such as mycophenolate mofetil, and cyclosporine.

Suitable antibacterial agents include antibiotics such as amoxicillin, meropenem and clavulanic acid.

Suitable LHRH agonists include goserelin acetate, deslorelin and leuprorelin.

Suitable LHRH antagonists include cetrorelix, ganirelix, abarelix and degarelix.

Suitable antiviral agents include nucleoside analogs such as lamivudine, zidovudine, abacavir and entecavir and suitable antiretro viral drugs include protease inhibitors such as atazanavir, lapinavir and ritonavir. Suitable selective estrogen receptor modulators include raloxifene and fulvestrant.

Suitable somastatin mimics include octreotide.

Suitable anti-inflammatory drugs include mesalazine and suitable NSAIDs include acetaminophen (paracetamol).

Suitable vitamin $D_2$ analogues include paricalcitol.

Suitable synthetic thyroxines include levothyroxine.

Suitable anti-histamines include fexofenadine.

Suitable antifungal agents include azoles such as viriconazole.

Suitable antioxidants include ascorbic acid, hydroxy carotenoids such as retinol, and calciferol.

Suitable anesthetics include propofol.

The complex alcohol may also be a solvent, such as, for example, tetraglycol and lauryl alcohol.

In some embodiments, the complex alcohol is sparingly soluble or insoluble in aqueous solution. For example, the complex alcohol may be farnesol.

In some embodiments, the complex alcohol may be a mixture of two or more complex alcohols.

In the above embodiments, the linear, branched or cyclic complex alcohol is monohydroxy or polyhydroxy. In some embodiments, the polyhydroxy complex alcohol comprises 2 hydroxy groups. In other embodiments, the polyhydroxy complex alcohol comprises more than 2 hydroxy groups. For example, the polyhydroxy complex alcohol may comprise 3, 4 or 5 hydroxy groups. In particular embodiments, the complex alcohol is a monohydroxy complex alcohol.

In the above embodiments, the linear, branched or cyclic complex alcohol may be unsubstituted or substituted with one or more substituent groups. Unless otherwise defined, the term "substituted" or "substituent" as used herein refers to a group which may or may not be further substituted with one or more groups selected from $C_{1-6}$alkyl, $C_{1-6}$alkenyl, $C_{1-6}$alkynyl, aryl, aldehyde, halogen, halo$C_{1-6}$alkyl, halo$C_{1-6}$alkenyl, halo$C_{1-6}$alkynyl, haloaryl, hydroxy, $C_{1-6}$alkylhydroxy, $C_{1-6}$alkoxy, —O$C_{1-6}$alkylhydroxy, —O$C_{1-6}$alkyl$C_{1-6}$alkoxy, $C_{1-6}$alkenyloxy, aryloxy, benzyloxy, halo$C_{1-6}$alkoxy, halo$C_{1-6}$alkenyloxy, haloaryloxy, nitro, nitro$C_{1-6}$alkyl, nitro$C_{1-6}$alkenyl, nitro$C_{1-6}$alkynyl, nitroaryl, nitroheterocyclyl, amino, $C_{1-6}$alkylamino, $C_{1-6}$dialkylamino, $C_{1-6}$alkenylamino, $C_{1-6}$alkynylamino, arylamino, diarylamino, benzylamino, dibenzylamino, acyl, $C_{1-6}$alkenylacyl, $C_{1-6}$alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy, mercapto, $C_{1-6}$alkylthio, benzylthio, acylthio, and phosphorus-containing groups.

Phosphorylation Reagent

The complex alcohol is mixed with $P_4O_{10}$. In some embodiments, the $P_4O_{10}$ may be partly hydrated (or a polyphosphoric acid).

The molar ratio of hydroxyl group (of the complex alcohol) to phosphorus may be within a range of about 3:1 to about 1:3. In some embodiments, the molar ratio is within the range of about 2:1 to about 1:2. In one embodiment, the molar ratio is about 2:1.

In another embodiment, the molar ratio is about 1:1, or substantially equimolar. In this particular embodiment, the molar ratio of hydroxyl group (of the complex alcohol) to $P_4O_{10}$ would be about 1:0.25.

Process

The process is for phosphorylating a complex alcohol, comprising the steps of:

(a) mixing the complex alcohol and $P_4O_{10}$ until its exothermic reaction temperature is achieved;

(b) allowing the reaction mixture of step (a) to react until the exothermic reaction is complete, and heating the reaction mixture of step (a) to within a range of at least about 90° C. to 140° C., if required;

(c) cooling the reaction mixture of step (b) to at least about 80° C.; and (d) hydrolysing the reaction mixture of step (c), wherein hydrolysis is conducted for about 30 to about 90 minutes.

Step (a)

This step involves mixing the complex alcohol and $P_4O_{10}$ until its exothermic reaction temperature is achieved.

The meaning of "exothermic reaction" is well known in the relevant art. It describes a chemical reaction that releases energy by light or, as in the present invention, heat. The term "exothermic reaction temperature" is used herein to refer to the temperature at which the chemical reaction between the complex alcohol and $P_4O_{10}$ commences to release heat.

The complex alcohol and $P_4O_{10}$ are mixed until its exothermic reaction temperature is achieved, and may be mixed to form an intimate mixture. Mixing may be achieved by any available means, including stirring (manual or mechanical). In some embodiments, mixing may also involve the use a high-shear mixer.

In some embodiments, this step may also involve heating the complex alcohol and $P_4O_{10}$ to advance the chemical reaction between the complex alcohol and $P_4O_1$oto its exothermic reaction temperature. For example, the complex alcohol and $P_4O_{10}$ may be heated so that its exothermic reaction temperature is achieved in a shorter period of time. For example, the complex alcohol and $P_4O_{10}$ may be heated to advance the chemical reaction between the complex alcohol and $P_4O_{10}$ to its exothermic reaction temperature in about 15 to 30 minutes.

In other embodiments, no heating is applied so that the chemical reaction between the complex alcohol and $P_4O_{10}$ achieves its exothermic reaction temperature over the time needed to reach this temperature.

Step (b)

This step involves allowing the reaction mixture of step (a) to react until the exothermic reaction is complete. In some embodiments, as the reaction progresses, heat is generated by the exothermic reaction process and the temperature of the reaction rises without external heating.

The exothermic reaction is complete when the temperature of the chemical reaction between the complex alcohol and $P_4O_{10}$ begins to fall.

If required, step (b) may involve heating if the temperature of the reaction mixture of step (a) is lower than about 90° C. after the exothermic reaction between the complex alcohol and $P_4O_{10}$ is complete. In one such embodiment, the reaction mixture of step (a) may be heated to within a range of at least about 90° C. to 140° C. In other such embodiments, the reaction mixture of step (a) may be heated to about 90° C., about 100° C., or about 110° C.

The temperature of the reaction mixture of step (a) may be maintained at the relevant temperature for about 30 to about 180 minutes. In some embodiments, the reaction mixture of step (a) is maintained at this temperature for about 60 to about 180 minutes. In one embodiment, the reaction mixture of step (a) is maintained at this temperature for about 60 to about 120 minutes. In another embodiment, the reaction mixture of step (a) is maintained at this temperature for about 60 minutes.

In some embodiments, this step does not involve mixing. In alternate embodiments, this step involves mixing. As mentioned above, mixing may be achieved by any available means, including stirring (manual or mechanical), and may also involve the use of a high-shear mixer.

Step (c)

This step involves cooling the reaction mixture of step (b) to at least 80° C.

In this step, the temperature is at least 80° C. The term "at least 80° C." is used herein to refer to a temperature equal to or greater than 80° C. In some embodiments, the temperature is within the range of at least 80° C. to about 160° C. In other embodiments, the temperature is within the range of about 90° C. to 140° C. In one embodiment, the temperature is about 90° C. In another embodiment, the temperature is about 100° C. In yet another embodiment, the temperature is about 110° C.

The reaction mixture of step (b) will be cooled to the relevant temperature if the temperature of the reaction mixture of step (b) is higher than this temperature after the exothermic reaction between the complex alcohol and $P_4O_{10}$ is complete.

In some embodiments, the cooling of the reaction mixture of step (b) may be allowed to proceed gradually over time. In other embodiments, the time may be limited to a specific period of time. For example, the period of time may be limited to about 30 to about 90 minutes, after which external means is used to further cool the reaction mixture of step (b).

Once at the cooled temperature, the reaction mixture of step (b) may be maintained at this temperature for about 30 to about 180 minutes. In some embodiments, the reaction mixture of step (b) is maintained at this temperature for about 60 to about 180 minutes. In one embodiment, the reaction mixture of step (b) is maintained at this temperature for about 60 to about 120 minutes. In another embodiment, the reaction mixture of step (b) is maintained at this temperature for about 60 minutes.

Step (d)

This step involves hydrolysing the reaction mixture of step (c).

Hydrolysis involves the addition of an aqueous solution. The aqueous solution may be water (e.g. deionised water). In some embodiments, an excess amount of water is added during the step of hydrolysis. During hydrolysis, the reaction mixture of step (c) may be maintained at the hydrolysis temperature of at least 80° C. The term "at least 80° C." has the meaning mentioned above. In some embodiments, the hydrolysis temperature is within the range of at least 80° C. to about 150° C. In some embodiments, the hydrolysis temperature is within the range of about 85° C. to 120° C. In one embodiment, the hydrolysis temperature is within the range of about 90° C. to 110° C. In another embodiment, the hydrolysis temperature is within the range of about 90° C. to 100° C. In yet another embodiment, the hydrolysis temperature is within the range of about 100° C. to 110° C.

Hydrolysis may be conducted for about 30 to about 180 minutes. In some embodiments, hydrolysis is conducted for about 30 to about 120 minutes. In some embodiments, hydrolysis is conducted for about 30 to about 90 minutes In one embodiment, hydrolysis is conducted for about 60 to about 120 minutes. In another embodiment, hydrolysis is conducted for about 90 to about 120 minutes. In one embodiment, hydrolysis is conducted for about 60 to about 90 minutes.

Optional Solvent

The process may be conducted in the absence of an additional solvent. The term "additional solvent" is used herein to refer to a solvent other than the aqueous solution, such as water, used during the step of hydrolysis. In some embodiments, the reaction is conducted without an additional solvent such that the complex alcohol and $P_4O_{10}$ are mixed in neat form.

Product

The invention also relates to a product obtained by the process.

The product obtained by the process may be a phosphorylated mono-complex alcohol, a phosphorylated di-complex alcohol, or a mixture thereof. In particular embodiments, the product is a mixture of a phosphorylated mono-complex alcohol and a phosphorylated di-complex alcohol. In these embodiments, the molar ratio of the mixture of the phosphorylated mono-complex alcohol and the phosphorylated di-complex alcohol may be at least about 2:1, about 2:1, about 6:4 or about 8:2, or within a range of about 4:1 to about 1:4 or about 6:4 to about 8:2.

In some embodiments, the product obtained by the process may be a cross-coupled phosphate diester.

It should be appreciated that the product obtained by the process may also comprise residual amounts of unreacted complex alcohol and/or related substances. In some embodiments, the product obtained by the process comprises unreacted complex alcohol in an amount of up to about 2% w/w. In some embodiments, the product obtained by the process comprises unreacted complex alcohol in an amount of up to about 1% w/w. In such embodiments, the process may further involve purification steps.

Further Process Steps to Obtain Further Products

The product obtained by the process may also be further reacted with an amphoteric surfactant.

In these embodiments, the complex alcohol is a tocopherol, and the phosphorylated complex alcohol is a tocopheryl phosphate. The tocopheryl phosphate may be a mono-tocopheryl phosphate, a di-tocopheryl phosphate, or a mixture thereof.

In one embodiment, the amphoteric surfactant is a tertiary amine of the formula $NR_1R_2R_3$, wherein $R_1$ is selected from the group consisting of $C_{6-22}$ alkyl, and $R_2$ and $R_3$ are independently selected from the group consisting of H, $(CH_2)_nCOOX$, $(CH_2)_nCHOHCH_2SO_3X$, $(CH_2)_nCHOHCH_2OPO_3X$, in which X is H or forms a salt with a cation selected from the group consisting of sodium, potassium, lithium, calcium, magnesium, ammonium, alkylammonium and alkanolamine, and n is 1 or 2.

The term "$C_{6-22}$ alkyl" refers to a straight or branched chain or cyclic hydrocarbon group having from 6 to 22 carbon atoms. Examples include, but are not limited to, hexyl, cyclohexyl, decyl, dodecyl, tridecyl, tetradecyl, pentadecyl, hexadecyl, heptadecyl and octadecyl.

In some embodiments, $R_1$ is a $C_{12}$ alkyl (dodecyl), and $R_2$ and $R_3$ are independently selected from $CH_2CH_2COOH$ and $CH_2CH_2COONa$.

In particular embodiments, the tertiary amine is 3-[2-carboxyethyl(dodecyl)amino] propanoic acid. In other embodiments, the tertiary amine is 3,3'-dodecylimino)dipropionic acid monosodium salt (or lauryliminodipropionic acid, sodium lauryliminodipropionate or N-lauryl iminodipropionate).

The product obtained by this further process may be lauryliminodipropionic acid tocopheryl phosphates or a salt thereof. In some embodiments, the salt is a sodium salt.

EXAMPLES

Various embodiments/aspects of the present invention will now be described with reference to the following non-limiting examples.

Example 1

Synthetic αc-tocopherol and $P_4O_{10}$ were mixed (mass ratio 0.170), and with heating, the exothermic reaction temperature was reached within about 15 minutes. Heating was continued until the reaction mixture a temperature of about 120° C. was achieved and then stopped. The temperature of the reaction mixture continued to rise for a brief period of time. When the exothermic reaction was complete, the reaction mixture was allowed to cool without any external control for about 60 minutes. The reaction was then further cooled to a temperature of about 90° C. before hydrolysis was conducted with deionised water for about 60 minutes.

The process produced about 58.52% w/w mono-tocopheryl phosphate and about 30.49% w/w di-tocopheryl phosphate.

It was also noted that there was about 0.21% w/w unreacted synthetic α-tocopherol.

Example 2

Synthetic α-tocopherol and $P_4O_{10}$ were mixed (mass ratio 0.170), and with heating, the exothermic reaction temperature was reached within about 15 minutes. Heating was continued until the reaction mixture a temperature of about 120° C. was achieved and then stopped. The temperature of the reaction mixture continued to rise for a brief period of time. When the exothermic reaction was complete, the reaction mixture was allowed to cool without any external control for about 60 minutes. The reaction was then further cooled to a temperature of about 90° C. before hydrolysis with deionised water was conducted for about 60 minutes.

The process produced about 59.26% w/w mono-tocopheryl phosphate and about 30.91% w/w di-tocopheryl phosphate.

It was also noted that there was about 0.20% w/w unreacted synthetic α-tocopherol.

Example 3

Natural α-tocopherol (0.07% w/w) and $P_4O_{10}$ were mixed (mass ratio 0.170), and with heating, the exothermic reaction temperature was reached within about 15 minutes. Heating was continued until the reaction mixture a temperature of about 120° C. was achieved and then stopped. The temperature of the reaction mixture continued to rise for a brief period of time. When the exothermic reaction was complete, the reaction mixture was allowed to cool without any external control for about 60 minutes. The reaction was then further cooled to a temperature of about 90° C. before hydrolysis with deionised water was conducted for about 60 minutes.

The process produced about 55.79% w/w mono-tocopheryl phosphate and about 27.68% w/w di-tocopheryl phosphate.

It was also noted that there was about 0.07% w/w unreacted synthetic α-tocopherol.

Example 4

Propofol (1.07 g, 6.00 mmol) and $P_4O_{10}$ (0.430 g, 1.51 mmol) were combined in a reaction tube and stirred vigorously. The reaction mixture was heated with a $H_2O$ bath (50-90° C.) for over 120 minutes so that the exothermic reaction was complete and then hydrolysed with $H_2O$ (0.260 g) at 90° C. for 60 minutes.

After cooling to room temperature the reaction mixture was dissolved in EtOH (30 mL), transferred to a 100 mL RBF and concentrated in vacuo (60° C. $H_2O$ bath). The residual red oily solid was suspended in hot hexane (90 mL) and filtered hot. The hexane filtrate was concentrated in vacuo (60° C. $H_2O$ bath) to ~25 mL and then cooled on an ice bath for about 120 minutes. The cold suspension was filtered in vacuo and the filter cake was washed with cold hexane (3×15 mL) and dried in a vacuum oven (55° C.) to give a white powder.

Mass spectrometry analysis of the end product indicated the formation of the desired monophosphate derivative of propofol.

Example 5

Propofol (0.565 g, 3.17 mmol), D-α-Tocopherol (1.35 g, 3.13 mmol) and $P_4O_{10}$ (0.462 g, 1.63 mmol) were combined in a Radleys 12 Station Carousel reaction tube. The reaction mixture was heated at 100° C. for 120 minutes to allow the respective exothermic reactions to complete. The reaction mixture was then cooled to 90° C. before hydrolysis with $H_2O$ (0.360 g) at that temperature for 60 minutes.

After cooling to room temperature, the reaction mixture was diluted with EtOH (30 mL), filtered and concentrated in vacuo (60° C. $H_2O$ bath) to give a brown oil substance.

Mass spectrometry analysis of the end product indicated the formation of the monophosphate derivatives of propofol and D-α-tocopherol, as well as the cross-coupled phosphate diester.

Example 6

Lauryl alcohol (0.990 g, 5.31 mmol) and $P_4O_{10}$ (0.530 g, 1.87 mmol) were combined in a Radleys 12 Station Carousel reaction tube and stirred vigorously. The reaction mixture was heated at 100° C. for 60 minutes and the exothermic reaction to complete. The reaction mixture was then cooled to 90° C. before hydrolysis with $H_2O$ (0.140 g) at that temperature for 60 minutes.

After cooling to room temperature, the reaction mixture was partitioned between $Et_2O$ (6 mL) and $H_2O$ (6 mL). The $Et_2O$ phase was concentrated in vacuo (60° C. $H_2O$ bath) to give a yellow liquid.

Mass spectrometry analysis of the end product indicated the formation of the desired monophosphate derivative of lauryl alcohol.

Example 7

β-Estradiol (0.490 g, 1.80 mmol) and $P_4O_{10}$ (0.140 g, 0.493 mmol) were combined in a Radleys 12 Station Carousel reaction tube and suspended in Triacetin (2 mL). The reaction mixture was heated at 100° C. for 60 minutes and to complete the exothermic reaction. The reaction mixture was then cooled to 90° C. before it was hydrolysed with $H_2O$ (1.00 g) at that temperature for 60 minutes.

After cooling to room temperature, the reaction mixture was washed with hexane (2×25 mL). The resultant suspension was dissolved in THF (30 mL) and concentrated in vacuo (60° C. $H_2O$ bath) to give an oily beige solid. Mass spectrometry analysis of the end product indicated the formation of the desired monophosphate derivative.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A process for phosphorylating tocopherol, comprising the steps of:
   (a) mixing the tocopherol and $P_4O_{10}$ until the mixture achieves an exothermic reaction temperature, said temperature being the temperature at which the chemical reaction between the tocopherol and $P_4O_{10}$ commences to release heat into the mixture;
   (b) allowing the reaction mixture of step (a) to react until the exothermic reaction is complete, wherein the exothermic reaction is complete when the temperature of the mixture comprising the chemical reaction between the tocopherol and $P_4O_{10}$ begins to fall;
   (c) cooling the reaction mixture of step (b) to at least 80° C.; and
   (d) hydrolysing the reaction mixture of step (c), wherein hydrolysis is conducted for 30 to 90 minutes.

2. The process of claim 1, wherein step (d) involves the addition of an aqueous solution.

3. The process of claim 1, wherein, in step (b) and/or (c), the temperature of the reaction mixture is maintained for 30 to 180 minutes, 60 to 180 minutes, 60 to 120 minutes, or 60 minutes.

4. The process of claim 1, wherein the temperature of the reaction mixture during the hydrolysis step (d) is at least 80° C., within the range of at least 80° C. to 150° C., within the range of 85° C. to 120° C., within the range of 90° C. to 110° C., within the range of 90° C. to 100° C., or within the range of 100° C. to 110° C.

5. The process of claim 1, wherein hydrolysis is conducted for 60 to 90 minutes.

6. The process of claim 1, wherein the product of the hydrolysis step (d) is a mixture of a phosphorylated mono-tocopherol and a phosphorylated di-tocopherol.

7. The process of claim 1, wherein the molar ratio of the mixture of the phosphorylated mono-tocopherol and the phosphorylated di-tocopherol is within a range of 6:4 to 8:2, or is 2:1.

* * * * *